United States Patent [19]

Hanahan et al.

[11] Patent Number: 4,504,474
[45] Date of Patent: Mar. 12, 1985

[54] SYNTHETIC PHOSPHOGLYCERIDES POSSESSING PLATELET ACTIVATING PROPERTIES

[75] Inventors: Donald J. Hanahan; R. Neal Pinckard, both of San Antonio, Tex.

[73] Assignee: Board of Regents, The University of Texas System, Austin, Tex.

[21] Appl. No.: 349,699

[22] Filed: Feb. 18, 1982

Related U.S. Application Data

[62] Division of Ser. No. 163,808, Jun. 27, 1980, Pat. No. 4,329,302.

[51] Int. Cl.$^3$ .................... C07F 9/10; A61K 31/685
[52] U.S. Cl. ...................... 514/78; 260/403; 514/114
[58] Field of Search ................ 260/403; 424/199, 211

[56] References Cited

U.S. PATENT DOCUMENTS

| | | | |
|---|---|---|---|
| 3,678,137 | 7/1972 | Pfeiffer | 260/944 |
| 3,694,473 | 9/1972 | Eibl et al. | 260/403 |
| 3,705,213 | 12/1972 | Pfeiffer et al. | 260/403 X |
| 3,708,558 | 1/1973 | Kny | 260/945 |
| 4,086,257 | 4/1978 | Sears | 260/403 |
| 4,159,988 | 7/1979 | Eibl et al. | 260/340.9 |

FOREIGN PATENT DOCUMENTS 54-106430  8/1979  Japan .................... 260/403

OTHER PUBLICATIONS

Acetyl Glyceryl Ether Phosphorylcholine: Platelet-Activating Factor, R. Neal Pinckard et al.
Chemistry and Biology of Acetyl Glyceryl Ether Phosphorylcholine (Platelet-Activating Factor), R. Neal Pinckard et al.
Hanahan, et al., Biochemistry 2:630–2:640 (1963).
Abstract TOYA*B05, 26406C/15*J5, 5028-955.
Blank et al., "Antihypertensive Activity of an Alkyl Ether Analog of Phosphatidycholine", *Biochemical and Biophysical Research Communications*, 90:1194–90:1200 (1979).
Demopoulos et al., J. Biol. Chem., vol. 254, No. 19, pp. 9355–9358 (10/10/1979).
Abstract TOYA*B05, 70927B/39*J5, 4106-430.

*Primary Examiner*—Thomas A. Waltz
*Attorney, Agent, or Firm*—Arnold, White and Durkee

[57] ABSTRACT

Novel synthetic glyceryl-phosphorylcholine compounds are prepared having biological activity paralleling that of naturally generated platelet activating factor.

2 Claims, No Drawings

SYNTHETIC PHOSPHOGLYCERIDES POSSESSING PLATELET ACTIVATING PROPERTIES

The Government has rights in the invention pursuant to National Institute of Health Grant No. HL-22555 awarded by the Department of Health, Education, and Welfare.

This is a division of Application Ser. No. 163,808, filed June 27, 1980, now U.S. Pat. No. 4,329,302.

BACKGROUND OF THE INVENTION

This invention relates to synthetic phosphoglyceride compounds, to methods of preparing such compounds, and to the use of such compounds in mediating platelet activation.

Applicants' have discussed background information relative to their invention in papers entitled "Platelet Activating Factor," 254 Journal of Biological Chemistry 9355-9358 (1979) and "Physicochemical and Functional Identity of Rabbit Platelet-Activating Factor (PAF) Released In Vivo During IgE Anaphylaxis with PAF Released In Vitro from IgE Sensitized Basophils," 123 Journal of Immunology 1847-1857 (1979). An Applicants' papers the elucidation of functional and physicochemical properties of PAF were explored.

The platelet, now recognized as an important cellular element involved in the acute inflammatory process, has been strongly implicated in a variety of immunologically mediated forms of tissue injury including immune complex deposition and IgE induced systemic anaphylactic shock. Platelet participation in these disease processes likely involves a cooperative cellular interaction where antigen stimulated IgE-sensitized basophils and presumably mast cells release a chemical mediator, platelet activating factor (PAF) which in turn interacts with the platelets inducing aggregation and secretion of granular constituents. As a further consequence of platelet activation there may result a fatal reaction consisting of acute pulmonary hypertension, right heart dilation, systemic hypertension, singificant increases in pulmonary vascular resistance, decreases in dynamic lung compliance and often complete pulmonary apnea.

The existence of a platelet activating factor was proposed in an article by Henson, P.M., 131 Journal of Experimental Medicine 287 (1970). Since that time the definition of its chemical structure and biochemical activity was not achieved due to the limited quanitities of material available for study.

One of the early reports on the chemical nature of PAF was that of Benveniste, J., 249 Nature 581 (1974). In this communication, Benveniste reported physicochemical characteristics of PAF to include a molecular weight of approximately 1100 daltons, a pI near 10 and an ability to bind to bovine serum albumin. A later study by Benveniste, J., et al, 269 Nature 170 (1977) reported the purification of PAF isolates by successive thin layer chromatography with chloroform: methanol: acetic acid: water as the solvent system. On the basis of a spray reaction, they concluded that PAF was a phospholipid.

Other studies exploring the physico-chemical characteristics of PAF suggested that PAF was a relatively small molecule having a molecular weight ranging from 300-500 daltons. Additionally, data suggested it was stable to freezing, stable to heating at 56° C. for 30 minutes, and stable at pH 3-10. No significant destruction by periodate, 2-mercaptoethanol and trypsin was noted, indicating PAF's resistance to oxidation, reduction and enzymatic attack respectively.

As more researchers released their findings certain inconsistencies became evident. For example the proposed molecular weight of PAF ranged from 300 to 1100 daltons. Moreover, one research group reported that PAF was inactivated by phospholipase D while another group reported suppression of PAF by phospholipase A and C but not by phospholipase D.

SUMMARY OF THE INVENTION

This invention relates to the synthesis of novel phosphoglycerides which exhibit platelet activating factor properties.

The invention contemplates a class of phosphoglycerides, particularly 1-O-alkyl ether phosphoglycerides and 1-O-fatty acyl phosphoglycerides (lysolecithin derivatives), which exhibit extremely potent biological activity towards washed rabbit platelets. The most active compound is 1-O-alkyl-2-acetyl-sn-glyceryl-3-phosphorylcholine (AGEPC), which demonstrates a biological activity indistinguishable from that of naturally generated rabbit platelet activating factor. Its biochemical and biological properties so closely parallel those of naturally occurring PAF, that it is proposed that are one and the same compound. Subsequent research by the Applicants has confirmed that AGEPC and PAF are the same composition (Hanahan et al., J. Bio. Chem. 255:5514–5516 (June 1980). The propionyl derivative of the ether glyceride series is nearly as potent, but the butyryl and longer chain fatty acid derivatives have relatively little or no activity. Comparable derivatives of the lysolecithin series, while having activity toward platelets, have significantly lower potency than the ether glyceride series.

The synthetic phosphoglycerides which are the subject of this invention are represented generally by the formula:

$$\begin{array}{c} \text{O} \quad \text{CH}_2\text{OR}_1 \\ \| \quad | \\ \text{R}_2\text{CO}-\text{CH} \quad \text{O} \\ | \quad \| \\ \text{CH}_2\text{OPOR}_3 \\ | \\ \text{O}^- \end{array}$$

wherein $R_1$ is a long chain carbonyl

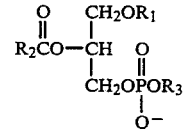

or a long chain alkyl $-(CH_2)_x CH_3$, wherein x denotes the integer 15 or 17; $R_2$ is a lower alkyl such as methyl, ethyl, or n-propyl; and $R_3$ is choline or amine bases thereof, such as

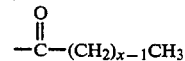

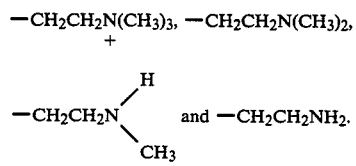

Synthetic approaches to preparation of the phosphoglycerides exhibiting platelet activating factor properties involve a chemical procedure wherein a naturally occurring precursor, easily isolated in high purity, can be used for final synthesis of AGEPC and related compounds. A precursor of the ether glyceride derivatives is lysoglycerylether phosphorylcholine obtained by hydrogenation of lysovinylglyceryl ether phosphorylcholine which is isolated from bovine heart tissue. A precursor of the fatty acyl derivatives is lysolecithin prepared through enzymatic action of phospholipase $A_2$ on purified egg lecithin. Next, small chain acyls are incorporated onto the 2-glyceryl position of each precursor. Of importance in each of these procedures in that a stereo-chemically well defined compound is synthesized. This facility to produce substantially optically pure compounds is of great importance in biological reactions.

DETAILED DESCRIPTION OF THE PREFERRED EMBODIMENTS

The following discussion is in terms of the preferred embodiments of this invention, which represent the best mode known to the inventors at the time of this application.

In accordance with the preferred embodiments of this invention a series of synthetic phosphoglycerides were developed having biological and biochemical characteristics analogous to endogenous PAF. The strategy culminating in the invention utilized the base sensitivity of PAF to investigate its possible resynthesis from the degradation products. The investigation revealed that acetylation of the products derived from base treatment of endogenous PAF produced a compound with high biological activity and an $R_f$ indistinguishable from that of the native PAF. Further, it was discovered that small chain acylation ($C_2$, $C_3$, $C_4$) of 1-acyl-sn-glyceryl-3-phosphorylcholine (lysolecithin) gave rise to glyceryl acyl phospholipids derivatives with platelet-activating behavior. While these lysolecithin derivatives functionally mimicked PAF, certain physiochemical properties differentiated and excluded them as being the native PAF molecule.

Further in accordance with such embodiments, small chain acylation ($C_2$, $C_3$, $C_4$) of the glyceryl ether phosphorylcholine, 1-O-alkyl-sn-glyceryl-3-phosphorylcholine, produced a class of glyceryl ether phospholipid chemical mediators having molar activities magnitudes of order greater than the lysolecithin derivatives. More particularly, acetylation of the precursor glyceryl ether phosphorylcholine yielded an exquisitely high activity platelet activating compound with biochemical properties identical to PAF. On the basis of further biochemical and functional tests to be discussed in the examples, Applicants' proposed and subsequently proved that 1-O-alkyl-2-acetyl-sn-glyceryl-3-phosphorylcholine (AGEPC) is structurally and biologically identical to native PAF.

According to the process of the present invention naturally occurring precursors easily isolated in high purity are subjected to methanolysis and subsequent reacylation for final synthesis of AGEPC and related compounds. More specifically, glyceryl ether phosphorylcholine obtained by hydrogenation of vinyl ether phosphorylcholine is subjected to base-catalyzed methanolysis, and subsequent reacylation utilizing low molecular weight acid anhydrides ($C_2$, $C_3$, $C_4$). Alternatively, lysolecithin derived from phospholipase $A_2$ treatment to egg lecithin is also subjected to acylation using low molecular weight acid anhydrides ($C_2$, $C_3$, $C_4$) forming a series of lysolecithin derivatives exhibiting platelet activating properties. The resulting series of synthetic phosphoglycerides which exhibit platelet activating properties are represented by the formula:

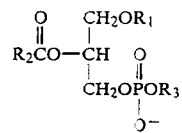

wherein $R_1$ is a long chain carbonyl

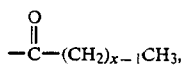

a long chain alkyl, $-(CH_2)_xCH_3$, wherein x denotes the integer 15 or 17; $R_2$ is a lower alkyl such as methyl, ethyl, or n-propyl; and $R_3$ is choline or amine base thereof selected from the group consisting of $$-CH_2CH_2\overset{+}{N}(CH_3)_3, \quad -CH_2CH_2N(CH_3)_2,$$

$$-CH_2CH_2\overset{+}{N}(CH_3)_3, \quad -CH_2CH_2N(CH_3)_2,$$

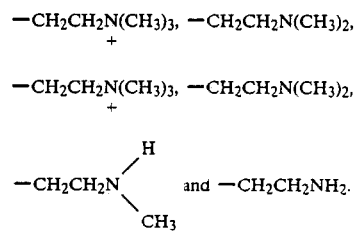

Of particular importance in the synthesis of biochemical mediators is that the process yields a stereochemically well defined product. In the present invention, the utilization of naturally occurring precursors ensures the optically pure configuration needed to accommodate many biochemically mediated reactions.

Isolation and purification of the purcursors, lysolecithin and vinyl ether-containing phospholipids have been described respectively in Wells, M. A., and Hanahan, D. J., 8 Biochemistry 414 (1969) and Pugh, E. L., et al., 18 Journal of Lipid Research 710 (1977).

Preparation and purification of endogenous PAF is described in Applicants' papers 254 Journal of Biological Chemistry 9355 (1979), 123 Journal of Immunology 1847 (1979), and Journal of Biological Chemistry 255:5514–5516 (June 1980).

The preferred embodiments of this invention are better illustrated by the examples which follow. In the examples the following materials and procedures were employed.

All solvents were ACS reagent grade or of the highest purity available. Acetic anhydride (99.7%) was a product of Fisher Scientific Co., propionic anhydride (97%) and butyric anhydride (99%) were purchased from Aldrich Chemical Co. Crystalline bovine serum albumin was obtained from Miles-Pentex.

Organic phosphorus was determined by the method of Bartlett, G., 234 Journal of Biochemistry 466 (1950). Gas-liquid chromatography was conducted on a Varian model 3700 gas chromatograph equipped with a 2 m × ¼ inch outer diameter stainless steel column containing 15% DEGS on Chromosorb AW 80/100. The temperature conditions were: column, 180° C.; flame ionization detector, 230° C.; and inlet, 220° C. Infrared spectra were obtained on a Beckman IR 4230 recording spectrophotometer using 1 mm NaCl cells.

Tyrode's, pH 7.2 was a buffer composed of 8 g/liter NaCl; 0.195 g/liter KCl; 1.02 g/liter NaHCO$_3$; 0.213 g/liter MgCl$_2$.6H$_2$O; 1.00 g/liter D-glucose; and 2.50 g/liter gelatin. The buffer was adjusted to pH 7.2 and contained 0.145 g/liter CaCl$_2$ (anhydrous).

In the following examples, Examples 1-6 illustrate the preferred methods of preparation of the subject composition invention. More particularly, Examples 1-3 describe the synthesis of the alkyl ether glyceride series while Examples 4-6 describe the synthesis of the fatty acyl glyceride (lysolecithin) series. Examples 7-15 depict a physiochemical (chromatographic migration) relationship among the invented synthetic phosphoglycerides and endogenous PAF. Further, Examples 16-23 describe various tests illustrating the applied uses of the novel series of phosphoglycerides.

EXAMPLE 1

Preparation of 1-O-alkyl-2-acetyl-sn-glyceryl-3-phosphorylcholine (AGEPC) and Amine Bases Thereof Vinyl ether-containing phospholipids of fresh beef heart were isolated and purified as outlined by Pugh et al, 18 J. Lipid Res. 710–716 (1977). Briefly, a fresh beef heart was cut up and coarsely ground. Meat was homogenized with methanol: chloroform (2:1 v/v) for 1 minute. The mixture was filtered and the filtrate was subjected to phase separation, using chloroform: water (1:1 v/v). The chloroform phase was concentrated in vacuo to dryness. The residual lipid material from the chloroform layer was dissolved in chloroform (50 ml) and stored at 4° C. The yield of total lipids was approximately 19.9 mg/g fresh tissue.

The choline containing fraction was further purified by thin layer chromatography using preparative (Analtech) Silica Gel G 1000µplates developed in a chloroform: methanol: water (65:35:6 v/v) solvent system.

The purified choline fraction was recovered by scraping the appropriate segment of the TLC plate and eluting the adsorbed choline fraction with chloroform: methanol: water (1:2:0.8 v/v). A portion of the eluted choline fraction was subjected to catalytic hydrogenation using PtO$_2$ as a catalyst at a hydrogen pressure of 60 p.s.i. for a period of three hours at room temperature. The resulting mixture of completely saturated choline containing phospholipids gave no reaction to Schiff base reagent indicating the absence of vinyl ethers or plasmalogens.

Further, the resulting mixture of completely saturated phosphorylcholines and amine bases thereof was subjected to short term base-catalyzed methanolysis, involving deacylation of the 2-glyceryl position in a chloroform-methanolic alkali medium. Specifically, the completely saturated phosphorylcholine mixture was treated with 0.5 N NaOH in a methanolchloroform mixture (10:1 v/v) for 2-3 minutes at 10° C. The reaction was quenched and neutralized by adjusting the reaction mixture to pH 7.

The resulting glyceryl ether phospholipids, 1-O-alkyl-sn-glyceryl-3-phosphorylcholine and amines bases thereof were isolated by thin layer chromatography (R$_f$ 0.15) using a solvent system of chloroform: methanol: water (65:35:6 v/v).

The isolated substrate contained 5.1% phosphorus and exhibited the following infrared pattern: 2930 cm$^{-1}$, 2860 cm$^{-1}$, 1460 cm$^{-1}$, 1375 cm$^{-1}$, —CH$_2$ and —CH$_3$; 1090 cm$^{-1}$, P-O; 1060 cm$^1$, P-O-C; 968 cm$^{-1}$, P-O-choline. The glyceryl ether composition (mole percent) was determined by gas-liquid chromatography wherein the ether linkage alkyl chain length was found to be 16:0 (78%) and 18:0 (22%).

Reacylation of the glyceryl ether analog was accomplished by dissolving the glyceryl ether analog in chloroform and adding acetic acid anhydride in a ratio of one part ether substrate and five parts acid anhydride. This reaction mixture was warmed in a 60° C. water bath for 45 minutes. After cooling to room temperature, separation of the reaction product, 1-O-alkyl-2-acetyl-sn-glyceryl-3-phosphorylcholine (AGEPC) and amine bases thereof was achieved through phase separation by mixing chloroform, methanol, and water with the reaction mixture. The chloroform rich layer containing the AGEPC and amine bases thereof was washed with methanol: water (10:9 v/v) until the chloroform layer was acid free. The product AGEPC and amine bases thereof was further purified by thin layer chromatography using chloroform: methanol: water (65:35:6 v/v).

EXAMPLE 2

Preparation of 1-O-alkyl-2-propionyl-sn-glyceryl-3-phosphorylcholine and Amine Bases Thereof Example 1 was repeated except that the specific anhydride used in the reacylation process was propionic acid anhydride.

EXAMPLE 3

Preparation of 1-O-alkyl-2-butyryl-sn-glyceryl-3-phosphorylcholine and Amine Bases Thereof Example 1 was repeated except that the specific anhydride used in the reacylation process was butyric acid anhydride.

EXAMPLES 4–6

Preparation of Lysolecithin Derivatives

Lysolecithin (1-acyl-sn-glyceryl-3-phosphorylcholine) and amine bases thereof were prepared through action of phospholipase A$_2$ on purified egg lecithin. Lysolecithin was recovered as a single band (R$_f$0.15) by thin layer chromatography using a solvent system of chloroform: methanol: water (65:35:6 v/v). Chemical analysis of the lysolecithin showed it contained 5.52% phosphorus and had an infrared spectrum with the following bands: 2925 cm$^{-1}$, 2855 cm$^{-1}$, 1458 cm$^{-1}$, —CH$_3$ and —CH$_2$; 1730 cm$^{-1}$, ester C=O; 1082 cm $^{-1}$, P-O$^{-1}$; 1055 cm$^{-1}$, P-O-C; 965 cm$^{-1}$, P-O-choline. Its fatty acid composition (mole percent) as determined by gas liquid chromatography was 16:0 (68%), 18:0 (27%) and 18:1 (4%).

Acylation of lysolecithin was accomplished by the acylation procedure outlined in Example 1 wherein a specific anhydride was reacted the substrate, lysolecithin and amine bases thereof. The products are tabulated below.

| Example | Specific Acid Anhydride | Product |
| --- | --- | --- |
| 4 | acetic acid anhydride | 1-acyl-2-acetyl-sn-glyceryl-3-phosphorylcholine and amine bases thereof |
| 5 | propionic acid anhydride | 1-acyl-2-propionyl-sn-glyceryl-3-phosphorylcholine and amine bases thereof |

-continued

| Example | Specific Acid Anhydride | Product |
|---|---|---|
| 6 | butyric acid anhydride | 1-acyl-2-butyryl-sn-glyceryl-3-phosphorylcholine and amine bases thereof |

The phosphorus content of the acetyl, propionyl, and butyryl derivatives ranged from 5.50 to 5.10%.

EXAMPLES 7-15

Chromatographic Comparison of Synthetic Phosphoglycerides with Endogenous PAF After the compounds in Examples 1-6 were synthesized, their behavior as compared to endogenous platelet activating factor (PAF) was studied through application on thin layer choromatography. These samples were developed for 50 minutes on a precoated Silica Gel G plate (250μ) (Analtech) in a solvent system of chloroform: methanol: ether (65:35:6 v/v). The spots were visualized by spraying the plate with concentrated sulfuric acid and charring.

Results were as follows:

| Example | Compound | $R_f$ |
|---|---|---|
| 7 | endogenous PAF (control) | 0.21 |
| 8 | 1-O—alkyl-2-acetyl-sn-glyceryl-3-phosphorylcholine | 0.21 |
| 9 | 1-O—alkyl-2-propionyl-sn-glyceryl-3-phosphorylcholine | 0.24 |
| 10 | 1-O—alkyl-2-butyryl-sn-glyceryl-3-phosphorylcholine | 0.30 |
| 11 | 1-acyl-2-acetyl-sn-glyceryl-3-phosphorylcholine | 0.21 |
| 12 | 1-acyl-2-proprionyl-sn-glyceryl-3-phosphorylcholine | 0.25 |
| 13 | 1-acyl-2-butyryl-sn-glyceryl-3-phosphorylcholine | 0.26 |
| 14 | lysolecithin (control) | 0.15 |
| 15 | sphingomyelin (control) | 0.23 |

Both the 1-O-alkyl-2-acetyl-sn-glyceryl-3-phosphorylcholine (AGEPC) and 1-acyl-2-acetyl-sn-glyceryl-2-phosphorylcholine (AcLL) migrated the same distance ($R_f$) as endogenous PAF. Each of the other derivatives has increasing $R_f$ values relative to the increasing -2-acyl-carbon length.

EXAMPLES 16-22

Comparison of Functional Activity of Endogenous PAF and Synthetic Phosphoglycerides A series of experiments were performed demonstrating the biological activities of the various synthetic phosphoglycerides with respect to their ability to induce dose-dependent platelet activation, as evidenced by platelet shape change without aggregation, platelet aggregation without serotonin secretion, and irreversible platelet aggregation with 50% secretion of serotonin (the latter measurement being defined as 1 unit of PAF-like activity).

The following procedure was employed to assess dose-dependent platelet activation as expressed by the various test parameters listed above. Preparation of washed $^3$H-serotonin-labeled rabbit platelets is described in Applicants' paper, 123 Journal of Immunology 1847 (1979).

Rabbit platelets internally labeled with $^3$H-serotonin (New England Nuclear; 28.2 Ci/mmol) were washed on Ficoll-Paque cushions and adjusted to $2.5 \times 10^8$ platelets/ml of Tyrode's buffer, pH 7.2. Appropriate dilutions of PAF or the test analogs were prepared in pyrogen-free 0.15 M NaCl containing 2.5 mg/ml of crystalline bovine serum albumin (albumin was required for PAF and test analog dispersion). Four microliters of the various dilutions of PAF and test analogs were added to 200 μl of prewarmed (37° C.) $^3$H-serotonin-labeled platelets in siliconized aggregometer cuvettes and the reaction mixture was incubated by slant stirring at 1200 rpm for 60 seconds. After the 60 second incubation, 20 μl of cold 1.5 M formaldehyde were added to stop the reactions. The cuvettes were immediately cooled to 0° C., centrifuged at 2200×g for 10 min. and the supernatants were assayed for percentage of $^3$H-serotonin secretion relative to 100% controls prepared by the addition of Triton X-100 (a nonionic detergent which induces complete non-specific rupture of platelets) to 200μl of the starting platelet suspension.

The percentage of serotonin secretion was determined by liquid scintillation spectroscopy relative to that released from the same volume of platelets after addition of 10 μl of 2.5% Triton X-100. The results were graphed linearly as the percent serotonin secretion versus the volume of test sample added. A 50% serotonin secretion endpoint was chosen to define 1 unit of PAF activitiy. Results of test samples were listed as molar concentration (mean ± standard deviation) equivalent to 1 functional unit of PAF activity. One unit of PAF activity was equivalent to $1 \times 10^{-10}$ M PAF.

Platelet aggregation and platelet shape change were both determined utilizing a Chronolog aggregometer at 37° C. with slant stirring (1200 rpm) of washed rabbit platelets and test sample mixture (500μl, 250,000 platelets /μl). The endpoint standard defined as the amount of test sample which resulted in a 50% increase in light transmission, as measured by the aggregometer.

Moreover, the platelet shape change with no aggregation was also determined according to the technique above. Since these test reactions are dose dependant, varying the concentration of test sample will produce a different platelet reaction. At the lowest concentration range of activity a test compound induces a platelet shape change, characterized by the platelet changing from the normal elliptical configuration to a circular configuration. When rotated on a central axis the normal elliptical platelet will allow light to pass similar to a strobe effect. However as the platelet changes to a circular configuration there is a decrease in light transmittance. It is the decrease in light transmittance which is assigned the endpoint of platelet shape change activity.

Results were as follows:

| Example | Compound | $^3$H—Serotonin release, 50%; M $\times 10^{-10}$ (mean ± stan. deviation) | Aggregation M $\times 10^{-10}$ | Shape Change M $\times 10^{-10}$ |
|---|---|---|---|---|
| 16 | PAF | 1.0 | 0.3 | 0.1 |
| 17 | 1-O—alkyl-2-acetyl sn-glyceryl-3- | 1.0 ± 0.3 | 0.3 | 0.1 |

| Example | Compound | $^3$H—Serotonin release, 50%; M × $10^{-10}$ (mean ± stan. deviation) | Aggregation M × $10^{-10}$ | Shape Change M × $10^{-10}$ |
|---|---|---|---|---|
| 18 | 1-O—alkyl-2-propionyl-sn-glyceryl-3-phosphorylcholine | 1.4 ± 0.4 | 0.3 | 0.1 |
| 19 | 1-O—alkyl-2-butyryl-sn-glyceryl-3-phosphorylcholine | 7.0 ± 2.0 | 10 | 6 |
| 20 | 1-acyl-2-acetyl-sn-glyceryl-3-phosphorylcholine | 240 ± 50 | 80 | 40 |
| 21 | 1-acyl-2-propionyl-sn-glyceryl-3-phosphorylcholine | 300 ± 60 | 70 | 30 |
| 22 | 1-acyl-2-butyryl sn-glyceryl-3-phosphorylcholine | Not active | Not Active | Not Active |

EXAMPLE 23

Native PAF and 1-O-alkyl-2-acetyl-sn-glyceryl-3-phosphorylcholine were utilized in cross-desensitization experiments to evaluate functional similarities. These experiments were based upon the observations that exposure of platelets to PAF under nonsecreting conditions (i.e., in absence of extracellular calcium) desensitized the platelets to a second exposure to PAF in the present of calcium. The desensitization is stimulus specific since serotonin secretion induced by other platelet stimulators not related to PAF, e.g., collagen or thrombin, was not decreased. Thus, platelets were desensitized to native PAF, AcLL or to AGEPC, and secretion profiles were determined upon control and desensitized platelets utilizing the native PAF, the synthetic phosphoglycerides, collagen and purified thrombin. $^3$H-serotonin-labeled platelets were resuspended in Tyrode's buffer, pH 7.2, containing 100 μM EGTA (ethylene glycol bis($\beta$-aminoethyl ether) N, N, N' , N' tetraacetic acid) and no calcium. The platelets were then divided into three portions to which was added either 10 units/ml of PAF, 10 units/ml of 1-O-alkyl-2-acetyl-sn-gylceryl-3-phosphorylcholine (AGEPC), or albumin-saline as a control. Following incubation at 37° C. for 20 minutes the platelets were washed twice prior to resuspension in Tyrode's buffer, pH 7.2, containing 1.3 ×$10^{-3}$ M calcium. The desensitized and control platelets then were tested for their respective reactivity to 1.0 units of native PAF, 1-O-alkyl-2-acetyl-sn-glyceryl-3-phosphorylcholine, 1-acyl-2-acetyl-sn-glyceryl-3-phosphorylcholine (AcLL), calf skin collagen (25 μg/ml. Worthington Biochemical Co.) or thrombin (purified α-thrombin 0.25 units/ml). Results were recorded as % $^3$H-serotonin release (mean ± standard deviation).

| Test stimulus | Desensitizing Agent | | |
|---|---|---|---|
| | Control | PAF | AGEPC |
| PAF | 50.4 ± 4.2 | 16.8 ± 9.6 | 16.8 ± 11.4 |
| AGEPC | 53.4 ± 0.3 | 15.7 ± 1.5 | 15.4 ± 6.1 |
| AcLL | 46.1 ± 5.4 | 12.1 ± 6.6 | 11.2 ± 6.6 |
| Collagen | 55.8 ± 4.3 | 57.5 ± 1.8 | 60.9 ± 1.1 |
| Thrombin | 64.3 ± 10.4 | 54.7 ± 9.3 | 66.6 ± 11.1 |

It can be seen that desensitization of platelets to native PAF also desensitized these cells to AGEPC and AcLL, but not to collagen or thrombin. In a similar fashion, desensitization of the platelets to AGEPC desensitized the platelets to AcLL and most importantly to native PAF. However, AGEPC did not desensitize platelets with respect to collagen or thrombin.

BRIEF DISCUSSION OF EXPERIMENTAL RESULTS

From the experiments reported as Examples 1–23 above, it was determined that insertion of a short chain fatty acid onto the 2-glyceryl position of either lysolecithin or 1-O-alkyl-sn-glyceryl-3-phosphorylcholine and amine bases thereof produced a compound with extremely potent biological activity toward washed rabbit platelets. The most active compound was 1-O-alkyl-2-acetyl-sn-glyceryl-3-phosphorylcholine (AGEPC). The propionyl derivative was nearly as potent, but the butyryl derivative had relatively little activity. Comparable derivative of the lysolecithin series, while having activity towards platelets, had significantly lower potency than the glyceryl ether series.

Though AGEPC is a synthetic compound, its existence in nature as platelet activating factor has been documented in Hanahan, et al., 255 J. Biol. Chem. 255:5514–5516 (June 1980). Several lines of evidence as shown in the examples support this conclusion. First both PAF and AGEPC have exactly the same $R_f$ values on thin layer chromatography. Treatment with base yielded in both AGEPC and PAF a biologically inactive product, giving rise to a chloroform-soluble component each of which migrated with the same $R_f$ value. Each of the base treated compounds described above upon treatment with acetic anhydride resulted in complete recovery of the initial biological activity. Additionally the products exhibited identical thin layer chromatography behavior with each other and native PAF. Thus on the foregoing data presented in the examples and in additional studies (255 J. Biol. Chem. 255:5514–5516 [June 1980]), it is concluded that naturally derived PAF and 1-O-alkyl-2-acetyl-sn-glyceryl-3-phosphorylcholine are one and the same compound.

Moreover, for optimum PAF activity it is concluded that there must be an ether linkage on position 1 of a sn-glyceryl-3-phosphorylcholine backbone and that a short chain fatty acid occupies position 2.

UTILITY

The methods described in the application are useful in large and small scale chemical synthesis. For example, such methods are useful in the pharmaceutical industry for the production of lipid mediators.

Further, other applications of the novel compounds include the utilization of these synthetic agents to modulate vascular permeability, inflammatory cell activation (including the platelet and neutrophil), desensitization of various inflammatory cell activity, smooth muscle contracting activity, hypotension, vasoconstriction and vasodilation, procoagulant activity, and initiation of prostaglandin biosynthesis.

While the invention has been described in terms of preferred embodiments constituting the best mode known to the Applicants at the time of this application, various changes may be made in the invention without departing from the scope thereof which is defined by the following claims.

What is claimed is:

1. A substantially pure glyceryl acyl phospholipid compound represented by the formula:

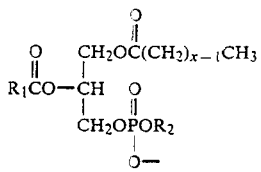

wherein
x denotes the integer 15 or 17;
$R_1$ is methyl, or ethyl; and
$R_2$ is an amine selected from the group consisting of

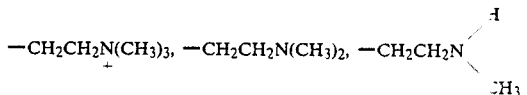

$-CH_2CH_2NH_2$ and pharmaceutically acceptable salts thereof.

2. A composition comprising an effective platelet activating amount of the compound recited in claim in combination with a pharamaceutically acceptable diluent.

* * * * *